(12) United States Patent
Qian

(10) Patent No.: US 11,906,532 B2
(45) Date of Patent: Feb. 20, 2024

(54) HEMOSTASIS MEASUREMENT DEVICE QUALITY CONTROL FORMULATIONS

(71) Applicant: Haemonetics Corporation, Boston, MA (US)

(72) Inventor: Xiaohua Qian, Sudbury, MA (US)

(73) Assignee: Haemonetics Corporation, Boston, MA (US)

( * ) Notice: Subject to any disclaimer, the term of this patent is extended or adjusted under 35 U.S.C. 154(b) by 141 days.

(21) Appl. No.: 17/703,354

(22) Filed: Mar. 24, 2022

(65) Prior Publication Data

US 2022/0317139 A1     Oct. 6, 2022

Related U.S. Application Data

(60) Provisional application No. 63/168,838, filed on Mar. 31, 2021.

(51) Int. Cl.
| | | |
|---|---|---|
| *G01N 31/00* | (2006.01) | |
| *G01N 33/53* | (2006.01) | |
| *G01N 33/96* | (2006.01) | |

(52) U.S. Cl.
CPC .................................. *G01N 33/96* (2013.01)

(58) Field of Classification Search
None
See application file for complete search history.

(56) References Cited

U.S. PATENT DOCUMENTS

| 6,194,394 B1 | 2/2001 | Hawkins |
|---|---|---|
| 7,012,132 B2 | 3/2006 | Lollar |
| 2003/0104508 A1 | 6/2003 | Gempeler et al. |
| 2006/0264779 A1 | 11/2006 | Kemp et al. |
| 2007/0020765 A1 | 1/2007 | Zander et al. |

FOREIGN PATENT DOCUMENTS

| WO | WO 1997/029792 | 8/1997 |
|---|---|---|
| WO | WO 2001/068109 | 9/2001 |

OTHER PUBLICATIONS

United States Patent and Trademark Office as the International Searching Authority, Authorized Officer: Kari Rodriquez, International Search Report and Written Opinion of the International Searching Authority, PCT/US22/21687, dated Sep. 6, 2022, 16 pages.

*Primary Examiner* — Lisa V Cook
(74) *Attorney, Agent, or Firm* — Nutter McClennen & Fish LLP

(57) ABSTRACT

Quality control formulations that do not require human donor-derived blood components for use in testing the efficacy of viscoelastic analysis reagents, and methods for preparing these formulations, are described.

20 Claims, 3 Drawing Sheets

HEMOSTASIS MEASUREMENT DEVICE QUALITY CONTROL FORMULATIONS

CROSS-REFERENCE TO RELATED APPLICATIONS

The present application claims priority from U.S. Provisional Application No. 63/168,838 filed Mar. 31, 2021, the disclosure of which is incorporated by reference herein in its entirety.

TECHNICAL FIELD

The present invention relates to quality control formulations for use in testing the efficacy of viscoelastic analysis reagents and methods for preparing these formulations.

BACKGROUND ART

Viscoelastic analysis is crucial in assessing patient blood samples in a wide variety of medical situations. It is therefore essential that reagents used for viscoelastic analysis provide accurate results when used in hospitals and clinical labs, for example. In order to ensure that these reagents provide accurate and reliable results, it is important that quality control tests be performed on them before they reach the end user.

Current formulations for performing quality control testing of viscoelastic analysis reagents require a human donor, containing human blood, human plasma, or components obtained from human blood, e.g., human red blood cells. The use of quality control formulations having human donor-derived blood components is relatively costly and poses a risk of infection to the donors.

There is therefore a need for a reliable quality control formulation for testing viscoelastic analysis reagents that does not contain human donor-derived blood components.

SUMMARY OF THE EMBODIMENTS

In accordance with one embodiment of the invention, a method of preparing a formulation for testing an efficacy of at least one viscoelastic analysis reagent, the formulation having a target bovine citrated plasma concentration, a target human tissue factor concentration, and a target heparin concentration, is provided. The method comprises a) determining the target concentration of bovine citrated plasma for the formulation by preparing a series of bovine citrated plasma dilutions, the series of bovine citrated plasma dilutions having at least two members; measuring a first viscoelastic characteristic for each member of the series of bovine citrated plasma dilutions to obtain a first value for each member of the series of bovine citrated plasma dilutions, said first viscoelastic characteristic having a target value; calculating a first linear regression from the first value for each member of the series of bovine citrated plasma dilutions; and extrapolating a predicted bovine citrated plasma concentration corresponding to the first viscoelastic characteristic target value from the first linear regression, the predicted bovine citrated plasma concentration being the target bovine citrated plasma concentration. The method further comprises b) determining the target concentration of human tissue factor for the formulation by preparing a series of human tissue factor dilutions, the series of human tissue factor dilutions having at least two members; measuring a second viscoelastic characteristic for each member of the series of human tissue factor dilutions to obtain a second value for each member of the series of human tissue factor dilutions, said second viscoelastic characteristic having a target value; calculating a second linear regression from the second value for each member of the series of human tissue factor dilutions; and extrapolating a predicted human tissue factor concentration corresponding to the second viscoelastic characteristic target value from the second linear regression, the predicted human tissue factor concentration being the target human tissue factor concentration. The method also comprises c) determining the target concentration of heparin for the formulation by preparing a series of heparin dilutions, the series of heparin dilutions having at least two members, measuring a third viscoelastic characteristic for each member of the series of heparin dilutions to obtain a third value for each member of the series of heparin dilutions, said third viscoelastic characteristic having a target value, calculating a third linear regression from the third value for each member of the series of heparin dilutions; and extrapolating a predicted heparin concentration corresponding to the third viscoelastic characteristic target value from the third linear regression, the predicted heparin concentration being the target heparin concentration. The method additionally comprises preparing the formulation by combining the bovine citrated plasma, human tissue factor, and heparin together such that the formulation comprises the bovine citrated plasma at the target bovine citrated plasma concentration, the human tissue factor at the target human tissue factor concentration, and the heparin at the target heparin concentration.

In some embodiments, steps b) and c) may be performed concurrently.

In some embodiments, in step (a), each member of the series of bovine citrated plasma dilutions has a bovine citrated plasma concentration, the concentration of bovine citrated plasma in any one member of the series of bovine citrated plasma dilutions being different than the concentration of bovine citrated plasma in any other member of the series of bovine citrated plasma dilutions, and each member of the series of bovine citrated plasma dilutions has a human tissue factor concentration, the human tissue factor concentration of each member of the series of bovine citrated plasma dilutions being the same. In step (b), each member of the series of human tissue factor dilutions has a human tissue factor concentration, the concentration of human tissue factor in any one member of the series of human tissue factor dilutions being different than the concentration of human tissue factor in any other member of the series of human tissue factor dilutions, each member of the series of human tissue factor dilutions has a bovine citrated plasma concentration, the bovine citrated plasma concentration of each member of the series of human tissue factor dilutions being the target bovine citrated plasma concentration, and each member of the series of human tissue factor dilutions has a heparin concentration, the heparin concentration of each member of the series of human tissue factor dilutions being the same. In step (c), each member of the series of heparin dilutions has a heparin concentration, the concentration of heparin in any one member of the series of heparin dilutions being different than the concentration of heparin in any other member of the series of heparin dilutions, each member of the series of heparin dilutions has a bovine citrated plasma concentration, the bovine citrated plasma concentration of each member of the series of heparin dilutions being the target bovine citrated plasma concentration, and each member of the series of heparin dilutions has a human tissue factor concentration, the human tissue factor concentration of each member of the series of heparin dilutions being the target human tissue factor concentration.

In other embodiments, in step (a), each member of the series of bovine citrated plasma dilutions has a bovine citrated plasma concentration, the concentration of bovine citrated plasma in any one member of the series of bovine citrated plasma dilutions being different than the concentration of bovine citrated plasma in any other member of the series of bovine citrated plasma dilutions, and each member of the series of bovine citrated plasma dilutions has a human tissue factor concentration, the human tissue factor concentration of each member of the series of bovine citrated plasma dilutions being the same. In step (c), each member of the series of heparin dilutions has a heparin concentration, the concentration of heparin in any one member of the series of heparin dilutions being different than the concentration of heparin in any other member of the series of heparin dilutions, each member of the series of heparin dilutions has a bovine citrated plasma concentration, the bovine citrated plasma concentration of each member of the series of heparin dilutions being the target bovine citrated plasma concentration, and each member of the series of heparin dilutions has a human tissue factor concentration, the human tissue factor concentration of each member of the series of heparin dilutions being the same. In step (b), each member of the series of human tissue factor dilutions has a human tissue factor concentration, the concentration of human tissue factor in any one member of the series of human tissue factor dilutions being different than the concentration of human tissue factor in any other member of the series of human tissue factor dilutions, each member of the series of human tissue factor dilutions has a bovine citrated plasma concentration, the bovine citrated plasma concentration of each member of the series of human tissue factor dilutions being the target bovine citrated plasma concentration, and each member of the series of human tissue factor dilutions has a heparin concentration, the heparin concentration of each member of the series of human tissue factor dilutions being the target heparin concentration.

In accordance with another embodiment of the invention, a method of preparing a formulation for testing an efficacy of at least one viscoelastic analysis reagent, the formulation having a target concentration of bovine citrated plasma, a target concentration of human tissue factor, and a target concentration of heparin, is provided. The method comprises a) determining the target concentration of bovine citrated plasma for the formulation by measuring a first viscoelastic characteristic for a bovine citrated plasma dilution to obtain a first value for the bovine citrated plasma dilution, said first viscoelastic characteristic having a target value, and determining a predicted bovine citrated plasma concentration based on the first value and corresponding to the first viscoelastic characteristic target value, the predicted bovine citrated plasma concentration being the target bovine citrated plasma concentration; and b) determining the target concentration of human tissue factor for the formulation by measuring a second viscoelastic characteristic for a human tissue factor dilution to obtain a second value for the human tissue factor dilution, said second viscoelastic characteristic having a target value, and determining a predicted human tissue factor concentration based on the second value and corresponding to the second viscoelastic characteristic target value, the predicted human tissue factor concentration being the target human tissue factor concentration; c) determining the target concentration of heparin for the formulation by measuring a third viscoelastic characteristic for a heparin dilution to obtain a third value for the heparin dilution, said third viscoelastic characteristic having a target value, and determining a predicted heparin concentration based on the third value and corresponding to the third viscoelastic characteristic target value, the predicted heparin concentration being the target heparin concentration; and d) preparing the formulation by combining the bovine citrated plasma, the human tissue factor, and the heparin together such that the formulation comprises the bovine citrated plasma at the target bovine citrated plasma concentration, the human tissue factor at the target human tissue factor concentration, the heparin at the target heparin concentration.

In some embodiments, steps b) and c) may be performed concurrently.

In accordance with another embodiment of the invention, a method of preparing a formulation for testing an efficacy of at least one viscoelastic analysis reagent, the formulation having a target bovine citrated plasma concentration, a target human tissue factor concentration, and a target heparin concentration. The method comprises determining the target bovine citrated plasma concentration for the formulation by a) preparing a series of bovine citrated plasma dilutions, the series of bovine citrated plasma dilutions having at least two members, measuring a first viscoelastic characteristic for each member of the series of bovine citrated plasma dilutions to obtain a first value for each member of the series of bovine citrated plasma dilutions, said first viscoelastic characteristic having a target value, calculating a first linear regression from the first value for each member of the series of bovine citrated plasma dilutions, and extrapolating a predicted bovine citrated plasma concentration corresponding to the first viscoelastic characteristic target value from the first linear regression, the predicted bovine citrated plasma concentration being the target bovine citrated plasma concentration; b) determining the target human tissue factor concentration and the target heparin concentration for the formulation by preparing a human tissue factor dilution set, the human tissue factor dilution set having at least two series of heparin dilutions, each series of heparin dilutions having at least two members, wherein each member of each series of heparin dilutions has a human tissue factor concentration and a heparin concentration, measuring a second viscoelastic characteristic for each member of each series of heparin dilutions to obtain a second value for each member of each series of heparin dilutions, said second viscoelastic characteristic having a target value, identifying a select member from the human tissue factor dilution set having a measured second viscoelastic characteristic nearer the second viscoelastic characteristic target value than any other member of the human tissue factor dilution set, the human tissue factor concentration of the select member being the target human tissue factor concentration and the heparin concentration of the select member being the target heparin concentration; and c) preparing the formulation by combining the bovine citrated plasma, human tissue factor, and heparin together such that the formulation comprises the bovine citrated plasma at the target bovine citrated plasma concentration, the human tissue factor at the target human tissue factor concentration, and the heparin at the target heparin concentration.

In some embodiments, in step (a), each member of the series of bovine citrated plasma dilutions has a bovine citrated plasma concentration, the concentration of bovine citrated plasma in any one member of the series of bovine citrated plasma dilutions being different than the concentration of bovine citrated plasma in any other member of the series of bovine citrated plasma dilutions, and each member of the series of bovine citrated plasma dilutions has a human tissue factor concentration, the human tissue factor concentration of each member of the series of bovine citrated plasma dilutions being the same. In step (b), each member of each series of heparin dilution has a bovine citrated plasma concentration, the bovine citrated plasma concentration of each member of each series of heparin dilutions being the target bovine citrated plasma concentration, the concentration of human tissue factor in any one series of heparin dilutions being different than the concentration of human tissue factor in any other series of heparin dilutions, the concentration of human tissue factor in every member of any one series of heparin dilutions being the same, and the concentration of heparin in any one member of any one series of heparin dilutions being different than the concentration of heparin in any other member of the same series of heparin dilutions.

The first, second, and/or third viscoelastic characteristic may be measured using a device for viscoelastic analysis. The device for viscoelastic analysis may be a microfluidic cartridge.

The first viscoelastic characteristic may be MA and the first viscoelastic characteristic target value may be about 63. The second viscoelastic characteristic may be R and the second viscoelastic characteristic target value may be about 6. The third viscoelastic characteristic may be R and the third viscoelastic characteristic target value may be about 6.

In accordance with one embodiment of the invention, a formulation for testing an efficacy of at least one viscoelastic analysis reagent, the formulation comprising 60-90% bovine citrated plasma, 0.05-0.20% human tissue factor, and 0.05-0.30 U/ml heparin.

In some embodiments, the formulation may comprise a stabilizing agent. The stabilizing agent may be glycine or HEPES buffer. The formulation may comprise a preservative. The preservative may be sodium azide. The pH of the formulation may be about 7.3 to about 7.9. The total protein content of the formulation may be greater than about 6.4 g/dL.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
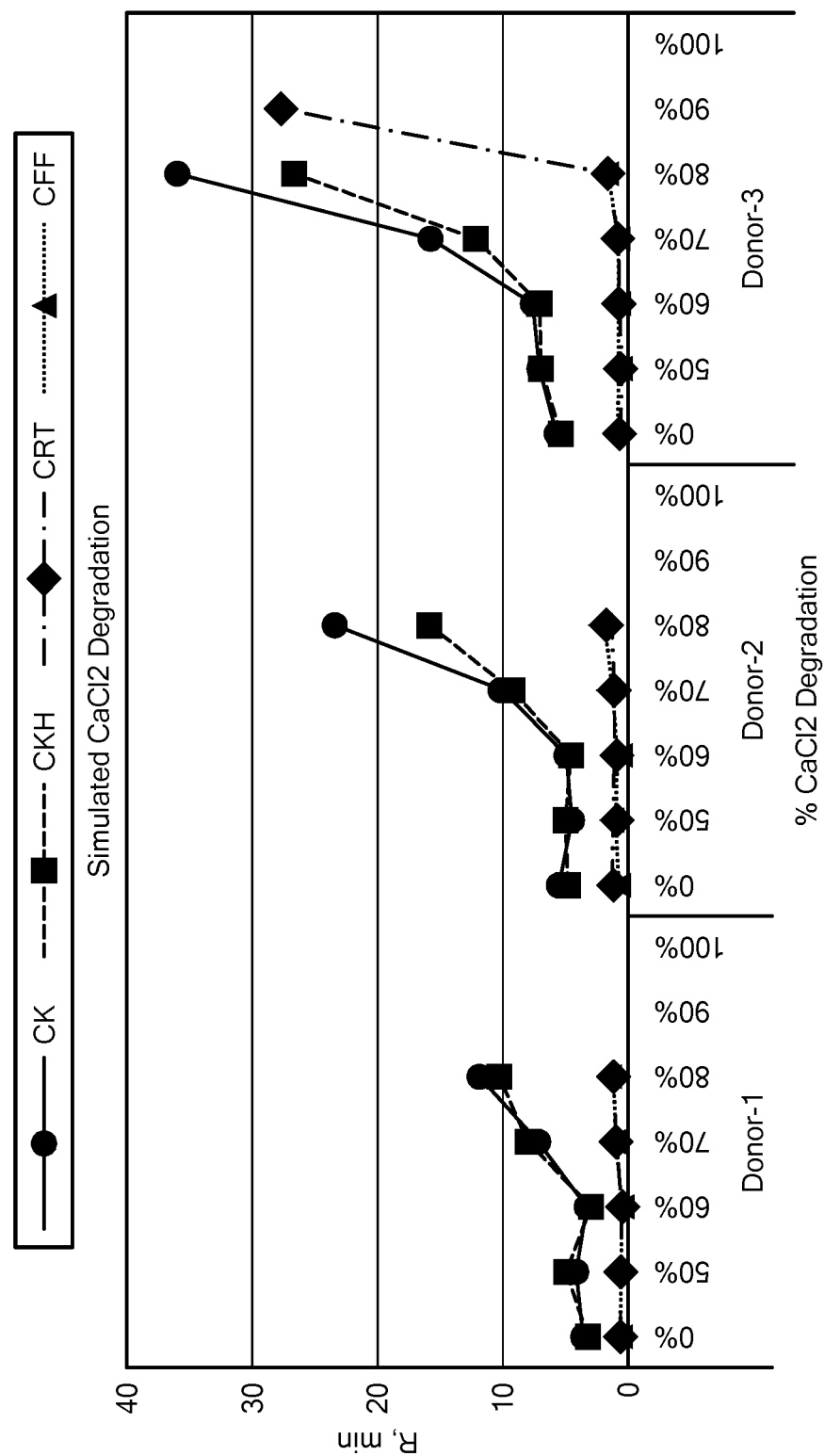
FIG. 1 shows TEG Global Hemostasis cartridge results obtained using human donor blood under conditions of simulated degradation of $CaCl_2$), in accordance with embodiments of the invention.

Definitions. As used in this description and the accompanying claims, the following terms shall have the meanings indicated, unless the context otherwise requires:

"About," in reference to a numerical value, shall mean the recited numerical value±10%.

"Viscoelastic analysis" shall mean any analysis method that measures the characteristics of elastic solids (e.g., fibrin solids) and fluids. In other words, viscoelastic analysis allows the study of properties of a viscous fluid, such as blood, plasma, or a blood sample. In some embodiments, the viscoelastic analysis is performed under conditions that mimic the conditions in vivo that result in hemostasis. For example, the condition may include a temperature that mimics a body temperature (e.g., a temperature of 37° C.). The condition may also include clot formation and dissolution at flow rates that mimic those found in blood vessels. Viscoelastic analysis encompasses, without limitation, viscoelastic assays and clotting assays such as thromboelastography (TEG), thromboelastometry (TEM), and those performed using microfluidic cartridges, for example, TEG Global Hemostasis assay cartridges suitable for use with the TEG 6s Hemostasis Analyzer system (Haemonetics, Corp., Boston, MA).

"Viscoelastic characteristic," "parameter," "clotting measurement," and the like, shall mean a measurement obtained through viscoelastic analysis, for example, a measurement of clot formation. This measurement can be taken any time during the formation of a clot including, without limitation, the time of the initial formation of fibrin or the time the clot achieves a certain level of strength.

One non-limiting example of a viscoelastic characteristic or parameter is the clot initiation time ("R"), which is the time of the initial formation of fibrin. Another non-limiting example of a viscoelastic characteristic or parameter is "MA" (maximum amplitude in mm), which is a direct function of the maximum dynamic properties of fibrin and platelet bonding and represents the ultimate strength of the fibrin-platelet clot. If the blood component tested has a reduced platelet function, MA represents the strength of the clot based on fibrin only. Viscoelastic characteristics can be measured on a blood component taken directly from subject, on a blood component that has been treated with a clotting activator such as kaolin, or on a blood component that has been treated with a clotting inhibitor such as citrate that has been suitably reversed by the addition of calcium.

A "device for viscoelastic analysis," and the like, shall mean an apparatus or device that can be used to measure viscoelastic characteristics of elastic solids and fluids, e.g., a device used in measuring the ability of blood or a blood component to form a clot. Microfluidic cartridges such as the TEG Global Hemostasis assay cartridges suitable for use with the TEG 6s Hemostasis Analyzer system (Haemonetics, Corp., Boston, MA) are a non-limiting example device for viscoelastic analysis.

"Viscoelastic analysis reagent," and the like, shall mean any compound, apart from a blood or plasma test sample, that is utilized in carrying out viscoelastic analysis on the test sample. Non-limiting examples of viscoelastic analysis reagents include calcium chloride ($CaCl_2$)), as well as biomolecules such as heparinase.

"Target value," and the like, as used herein shall mean the value (or range of values) of a viscoelastic characteristic or parameter for a particular clotting assay that is the preferred value for that particular assay when performed on a blood component from healthy subject, and using viscoelastic analysis reagents that have not degraded or lost their efficacy to an appreciable extent.

"Target concentration," and the like, as used herein shall mean the concentration of a component of a quality control formulation that, when present in a quality control formulation at this concentration, is determined or predicted to achieve the target value for a particular assay when the assay is performed with viscoelastic analysis reagents that have not degraded or lost their efficacy to an appreciable extent.

Quality control of reagents used for viscoelastic analysis of human blood, including devices containing such reagents, is essential for assuring that the end user obtains accurate viscoelastic analysis results. Viscoelastic clotting assays utilize reagents such as calcium chloride, as well as various biomolecules, e.g., heparinase. These reagents can degrade over time, causing the results obtained from their use to be inaccurate and unreliable.

Present quality control formulations for use in the testing of these reagents and reagent-containing devices require a human donor, and contain human blood, human plasma, or components obtained from human blood, e.g., human red blood cells. The use of quality control formulations containing human donor-derived blood components is relatively costly and poses a risk of infection to the donors. Furthermore, the use of human-derived blood components is less convenient to produce at scale.

The quality control formulations described herein for use in testing the efficacy of viscoelastic analysis reagents do not require a human donor for their manufacture. In some embodiments, the quality control formulations contain citrated bovine plasma, recombinant human tissue factor, and heparin (preferably low molecular weight heparin). In some embodiments, the quality control formulations further comprise at least one additional component selected from the group consisting of buffers, stabilizers, and preservatives. Instructions for the use of embodiments of the quality control formulations described herein are described in Appendix A, attached hereto and incorporated by reference herein in its entirety.

The viscoelastic analysis methods and assays described herein utilize reagent-containing TEG Global Hemostasis assay cartridges suitable for use with the TEG 6s Hemostasis Analyzer system. However, it will be appreciated by those of skill in the art that the methods and formulations described herein may also be applied using different viscoelastic analysis methods and clotting assays, and using different viscoelastic analysis devices.

The TEG Global Hemostasis assay cartridge ("TEG cartridge") is a citrated multi-channel microfluidic cartridge that provides four clotting assays that indicate the functional measurement of clotting factors, platelets and fibrinogen, and fibrinolysis. These four assays include (i) a kaolin assay ("CK"), which is an intrinsic activated assay that identifies hemostatic characteristics, the risk of bleeding, and thrombosis; (ii) a kaolin with heparinase assay ("CKH"), which eliminates the effect of heparin in the test sample and is used in conjunction with CK to assess the presence of systemic heparin or heparinoids; (iii) a RAPIDTEG' assay ("CRT"), incorporating both kaolin and tissue factor, which is an intrinsic and extrinsic pathway activated assay that is able to more rapidly assess patient hemostasis properties; and (iv) a functional fibrinogen assay ("CFF"), an extrinsic pathway activated assay that uses a GP IIb/IIIa platelet inhibitor to isolate fibrin contribution to clot strength and can be used along with CK to assess the relative contribution of platelets and fibrinogen to overall clot strength.

In some embodiments, quality control formulations of the present invention resulting in elongation of both CK R and CKH R times indicates that the amount/activity of $CaCl_2$) on the TEG cartridge is decreased to the degree that the cartridge, and other cartridges of the same lot, can no longer produce reliable results and, therefore, can no longer be used to test patient samples.

In some embodiments, heparin is included in the quality control formulations to separate CK R and CKH R. When CKH R values increase to more closely match CK R values, this indicates that the heparinase amount/activity on the cartridges is decreased to the degree that the cartridge, and other cartridges of the same lot, can no longer produce reliable results and, therefore, can no longer be used to test patient samples.

In some embodiments, methods are provided for preparing a quality control formulation having a target concentration of bovine citrated plasma, a target concentration of human tissue factor, and a target concentration of heparin, for testing the efficacy of at least one viscoelastic analysis reagent.

In some embodiments, the method includes determining the target concentration of bovine citrated plasma for the formulation by measuring a first viscoelastic characteristic, which has a target value, for a bovine citrated plasma dilution to obtain a first value for the bovine citrated plasma dilution. A predicted bovine citrated plasma concentration is determined based on the first value and corresponding to the first viscoelastic characteristic target value. The predicted bovine citrated plasma concentration is the target bovine citrated plasma concentration.

The method further includes determining the target concentration of human tissue factor for the formulation by measuring a second viscoelastic characteristic, which has a target value, for a human tissue factor dilution to obtain a second value for the human tissue factor dilution. A predicted human tissue factor concentration is determined based on the second value and corresponding to the second viscoelastic characteristic target value. The predicted human tissue factor concentration is the target human tissue factor concentration.

The method also includes determining the target concentration of heparin for the formulation by measuring a third viscoelastic characteristic, which has a target value, for a heparin dilution to obtain a third value for the heparin dilution. A predicted heparin concentration is determined based on the third value and corresponding to the third viscoelastic characteristic target value. The predicted heparin concentration is the target heparin concentration.

The formulation is then prepared by combining the bovine citrated plasma, the human tissue factor, and the heparin together such that the formulation comprises the bovine citrated plasma at the target bovine citrated plasma concentration, the human tissue factor at the target human tissue factor concentration, the heparin at the target heparin concentration.

In some embodiments, the method includes determining the target concentration of bovine citrated plasma for the formulation by preparing a series of bovine citrated plasma dilutions, the series of bovine citrated plasma dilutions having at least two members. A first viscoelastic characteristic, which has a target value, is measured for each member of the series of bovine citrated plasma dilutions to obtain a first value for each member of the series of bovine citrated plasma dilutions. A linear regression is calculated from the first value for each member of the series of bovine citrated plasma dilutions and a predicted bovine citrated plasma concentration is extrapolated from the linear regression that corresponds to the target value for the first viscoelastic characteristic. The predicted bovine citrated plasma concentration is the target bovine citrated plasma concentration.

The method further includes determining the target concentration of human tissue factor for the formulation by preparing a series of human tissue factor dilutions, the series of human tissue factor dilutions having at least two members. A second viscoelastic characteristic, which has a target value, is measured for each member of the series of human tissue factor dilutions to obtain a second value for each member of the series of human tissue factor dilutions. A linear regression is calculated from the second value for each member of the series of human tissue factor dilutions and a predicted human tissue factor concentration is extrapolated from the linear regression that corresponds to the target value for the second viscoelastic characteristic target value. The predicted human tissue factor concentration is the target human tissue factor concentration.

The method also includes determining the target concentration of heparin for the formulation by preparing a series of heparin dilutions, the series of heparin dilutions having at least two members. A third viscoelastic characteristic, which has a target value, is measured for each member of the series of heparin dilutions to obtain a third value for each member of the series of heparin dilutions. A linear regression is calculated from the third value for each member of the series of heparin dilutions and a predicted heparin concentration is extrapolated from the linear regression that corresponds to the target value for the third viscoelastic characteristic target value. The predicted heparin concentration is the target heparin concentration.

The formulation is then prepared by combining the bovine citrated plasma, the human tissue factor, and the heparin together such that the formulation comprises the bovine citrated plasma at the target bovine citrated plasma concentration, the human tissue factor at the target human tissue factor concentration, the heparin at the target heparin concentration.

When determining the target concentration of bovine citrated plasma, each member of the series of bovine citrated plasma dilutions has a different concentration of bovine citrated plasma, while each member of the series of bovine citrated plasma dilutions has a constant concentration of human tissue factor.

When determining the target concentration of human tissue factor, each member of the series of human tissue factor dilutions has a different concentration of human tissue factor, while each member of the series of human tissue factor dilutions has a bovine citrated plasma concentration that is the target bovine citrated plasma concentration, and constant concentration of heparin. In some embodiments, the constant concentration of heparin in each member of the series of human tissue factor dilutions is the target heparin concentration.

When determining the target concentration of heparin, each member of the series of heparin dilutions has a different concentration of heparin, while each member of the series of heparin dilutions has a bovine citrated plasma concentration that is the target bovine citrated plasma concentration, and constant concentration of human tissue factor. In some embodiments, the constant concentration of human tissue factor in each member of the series of heparin dilutions is the target human tissue factor concentration.

In some embodiments, the target concentration of human tissue factor and the target concentration of heparin may be determined at once by preparing a series of human tissue factor dilutions, each member of the series of human tissue factor dilutions having a different human tissue factor concentration and having a bovine citrated plasma concentration that is the target bovine citrated plasma concentration. Each member of the series of human tissue factor dilutions may then be split into several sub-members, each sub-member derived from a particular member and having a different heparin concentration.

One or more of the first viscoelastic characteristic, the second viscoelastic characteristic, and the third viscoelastic characteristic may be measured using a device for viscoelastic analysis. The device for viscoelastic analysis may include a microfluidic cartridge.

In some embodiments, the first viscoelastic characteristic is MA and the first viscoelastic characteristic target value is about 63. The first viscoelastic characteristic and first viscoelastic target value can be determined from CK clotting assays.

In some embodiments, at least one of the second viscoelastic characteristic and the third viscoelastic characteristic is R and at least one of the second viscoelastic characteristic and the third viscoelastic characteristic target value is about 6. In some embodiments, at least one of the second viscoelastic characteristic and the third viscoelastic characteristic target value is about 4. One or more of the second viscoelastic characteristic and third viscoelastic characteristic, and one or more of the second viscoelastic target value and third viscoelastic target value can be determined from CK and CKH clotting assays. When evaluating formulations comprising heparin using a clotting assay that does not utilize heparinase (such as CK), the target value is about 6 for the viscoelastic characteristic R. When evaluating formulations comprising heparin using a clotting assay that utilizes heparinase (such as CKH), the target value is 4 for the viscoelastic characteristic R. When evaluating formulations lacking heparin, the target value is about 4 for the viscoelastic characteristic R.

In some embodiments, a quality control formulation for testing an efficacy of at least one viscoelastic analysis reagent is provided, the formulation having 60-90% bovine citrated plasma, 0.05-0.20% human tissue factor, and 0.05-0.30 U/ml heparin.

The quality control formulation may further include one or more stabilizing agents well-known in the art, e.g., glycine, HEPES buffers, and other buffers well-known in the art.

The quality control formulation may further include one or more preservatives well-known in the art, e.g., sodium azide.

In some embodiments, the quality control formulation has a pH from about 7.3 to about 7.9. The total protein content of the formulation is preferably greater than about 6.4 g/dL.

EXAMPLES

Example 1: Preparation of Quality Control Formulation

A sample volume from a lot of bovine citrated plasma (BCP) (3.8% sodium citrate) was thawed in a water bath with water warm to the touch. 5 ml of 1M HEPES buffered saline (HBS) was added per 500 ml of BCP to obtain a 9.9 mM final HEPES concentration. The resulting solution was mixed for 5 minutes.

A series of trial formulations was then prepared, varying the concentration of BCP and with a constant concentration (0.05%) of Recombiplastin 2G (R2G), a recombinant human tissue factor. Viscoelastic analysis was performed on each formulation using TEG Global Hemostasis cartridges on the TEG6s Analyzer, the data which is shown in Table 1, below.

TABLE 1

| % BCP | MA, mm | | | | R, min | |
|---|---|---|---|---|---|---|
| | CK | CKH | CRT | CFF | CK | CKH |
| 60% | 50.7 | 49.8 | 47.0 | 47.0 | 3.4 | 3.3 |
| 70% | 57.6 | 57.0 | 52.6 | 53.3 | 3.1 | 3.1 |
| 80% | 61.4 | 61.1 | 56.3 | 58.8 | 3.3 | 3.3 |
| 90% | 65.6 | 64.5 | 60.4 | 62.5 | 3.9 | 3.7 |

Based on linear regression of the CK MA data, the target BCP concentration is predicted to be 83.6%, corresponding to the viscoelastic characteristic (MA) target value (63) for the CK assay.

A series R2G dilutions (using a 25% R2G working solution of R2G) and LOVENOX® (heparin) dilutions (using a 10 U/ml LOVENOX® working solution) were then prepared such that the final BCP concentration is the target BCP concentration (~83.6% based on the linear regression, above). These dilutions, including other buffers and stabilizers, is shown in Table 2.

TABLE 2

| Dilution # | Final % R2G | Final Lovenox® (U/ml) | 10% Glycine, ml | 25% R2G, ml | Lovenox®, ml | 99% BCP, ml | 1M HBS Buffer, ml | Total Vol, ml |
|---|---|---|---|---|---|---|---|---|
| 1 | 0.025% | 0.050 | 0.460 | 0.010 | 0.050 | 8.500 | 0.980 | 10.00 |
| 2 | 0.025% | 0.100 | 0.460 | 0.010 | 0.100 | 8.500 | 0.930 | 10.00 |
| 3 | 0.025% | 0.150 | 0.460 | 0.010 | 0.150 | 8.500 | 0.880 | 10.00 |
| 4 | 0.025% | 0.200 | 0.460 | 0.010 | 0.200 | 8.500 | 0.830 | 10.00 |
| 5 | 0.050% | 0.050 | 0.460 | 0.020 | 0.050 | 8.500 | 0.970 | 10.00 |
| 6 | 0.050% | 0.100 | 0.460 | 0.020 | 0.100 | 8.500 | 0.920 | 10.00 |
| 7 | 0.050% | 0.150 | 0.460 | 0.020 | 0.150 | 8.500 | 0.870 | 10.00 |
| 8 | 0.050% | 0.200 | 0.460 | 0.020 | 0.200 | 8.500 | 0.820 | 10.00 |
| 9 | 0.075% | 0.050 | 0.460 | 0.030 | 0.050 | 8.500 | 0.960 | 10.00 |
| 10 | 0.075% | 0.100 | 0.460 | 0.030 | 0.100 | 8.500 | 0.910 | 10.00 |
| 11 | 0.075% | 0.150 | 0.460 | 0.030 | 0.150 | 8.500 | 0.860 | 10.00 |
| 12 | 0.075% | 0.200 | 0.460 | 0.030 | 0.200 | 8.500 | 0.810 | 10.00 |
| 13 | 0.100% | 0.050 | 0.460 | 0.040 | 0.050 | 8.500 | 0.950 | 10.00 |
| 14 | 0.100% | 0.100 | 0.460 | 0.040 | 0.100 | 8.500 | 0.900 | 10.00 |
| 15 | 0.100% | 0.150 | 0.460 | 0.040 | 0.150 | 8.500 | 0.850 | 10.00 |
| 16 | 0.100% | 0.200 | 0.460 | 0.040 | 0.200 | 8.500 | 0.800 | 10.00 |

1 ml of each of the R2G/LOVENOX® dilutions from Table 2 was aliquoted into separate glass vials. The vials were frozen at ≤−35° C. and lyophilized the samples. Once the samples were lyophilized, each lyophilized R2G/LOVENOX® dilution was reconstituted with distilled deionized water.

Viscoelastic analysis was performed on each reconstituted R2G/LOVENOX® dilution using TEG Global Hemostasis cartridges on the TEG6s Analyzer.

From the viscoelastic analysis of the reconstituted R2G/LOVENOX® dilutions, it was determined that dilution #10, corresponding to an R2G concentration of 0.075% and a LOVENOX® concentration of 0.100 U/ml, provided CK R results, shown in Table 3, nearest the nominal CK assay R target value of 6.0, while also producing additional viscoelastic analysis results falling within the acceptance ranges shown in Table 4.

TABLE 3

| Dilution # | MA, mm | | | | R, min | | ΔR (CK−CKH) |
|---|---|---|---|---|---|---|---|
| | CK | CKH | CRT | CFF | CK | CKH | |
| 10 | 66.7 | 67.5 | 58.7 | 62.0 | 6.3 | 4.60 | 1.7 |

TABLE 4

| Viscoelastic Characteristic | Nominal Target Value | Acceptance Range |
|---|---|---|
| CK-R (min) | 6.0 | 4.6-9.1 (min) |
| CKH-R (min) | 4.0 | 3.6-6.0 (min) |
| CK-MA (mm) | 65 | 60-70 (mm) |
| CKH-MA (mm) | 65 | 60-70 (mm) |
| CRT-MA (mm) | 60 | 55-65 (mm) |
| CFF-MA (mm) | 60 | 55-65 (mm) |
| Delta-R (CK-CKH) | 1.5 | 1.0-2.5 |

Based on the results presented above, a quality control formulation having a target BCP concentration of ~83.6%, a target R2G concentration of 0.075%, and a target LOVENOX® concentration of 0.100 U/ml were chosen to proceed to the manufacturing process.

Example 2: Use of the Quality Control Formulations

Figure 2:
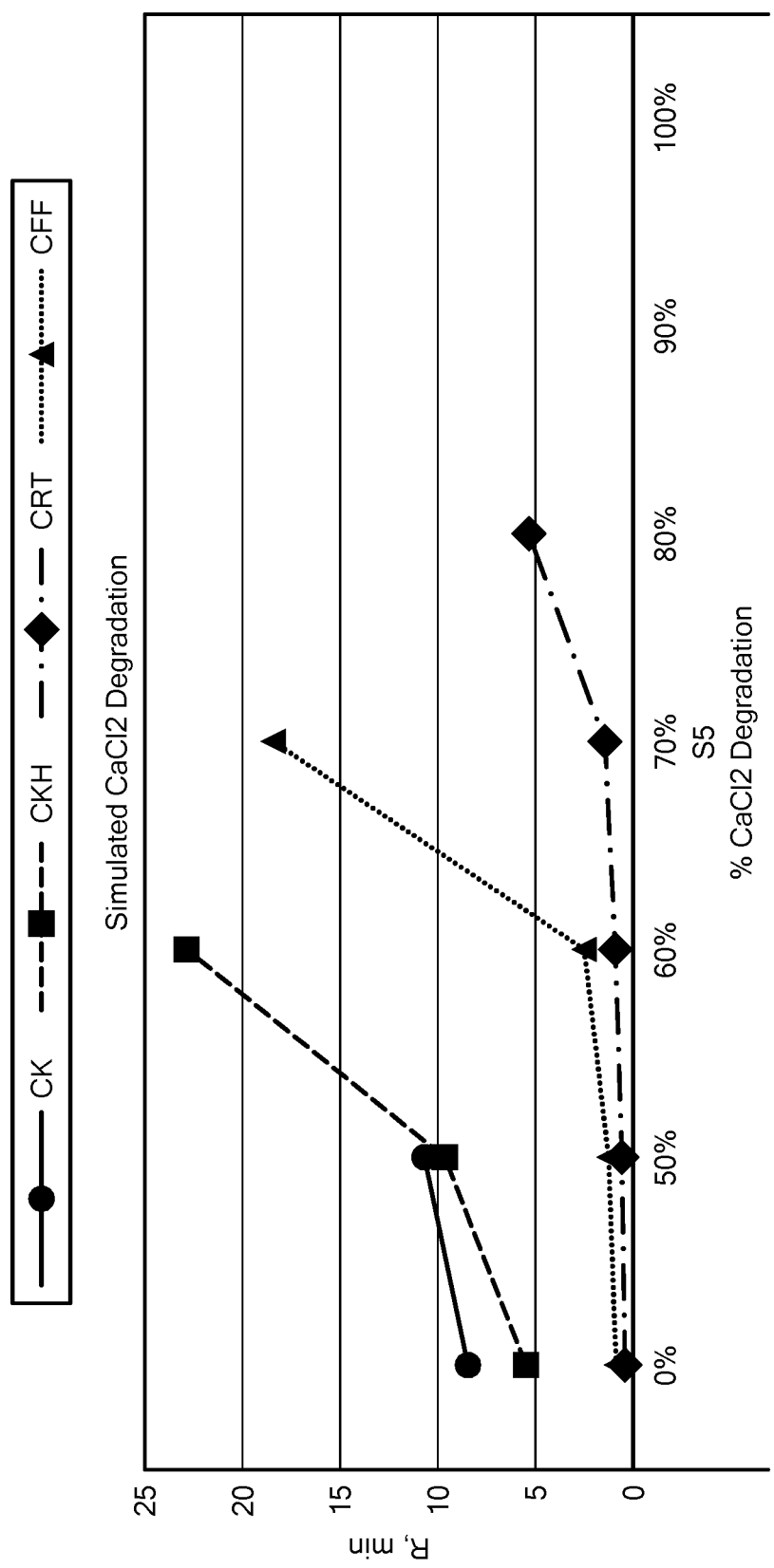
FIG. 2 shows TEG Global Hemostasis cartridge results obtained using quality control formulations described herein under conditions of simulated degradation of $CaCl_2$), in accordance with embodiments of the invention.

The quality control formulations described herein can be used to detect cartridge viscoelastic analysis reagent degradation. FIGS. 1 and 2 show a comparison of responses of human donor blood samples and quality control formulation samples described herein using TEG cartridges of varying simulated $CaCl_2$ (a critical component) degradation levels. It is evident that the quality control formulations can detect $CaCl_2$ degradation at 50%, above that level, R time on the CKH channel is significantly elongated, and no clotting happened on the CK channel.

Figure 3:
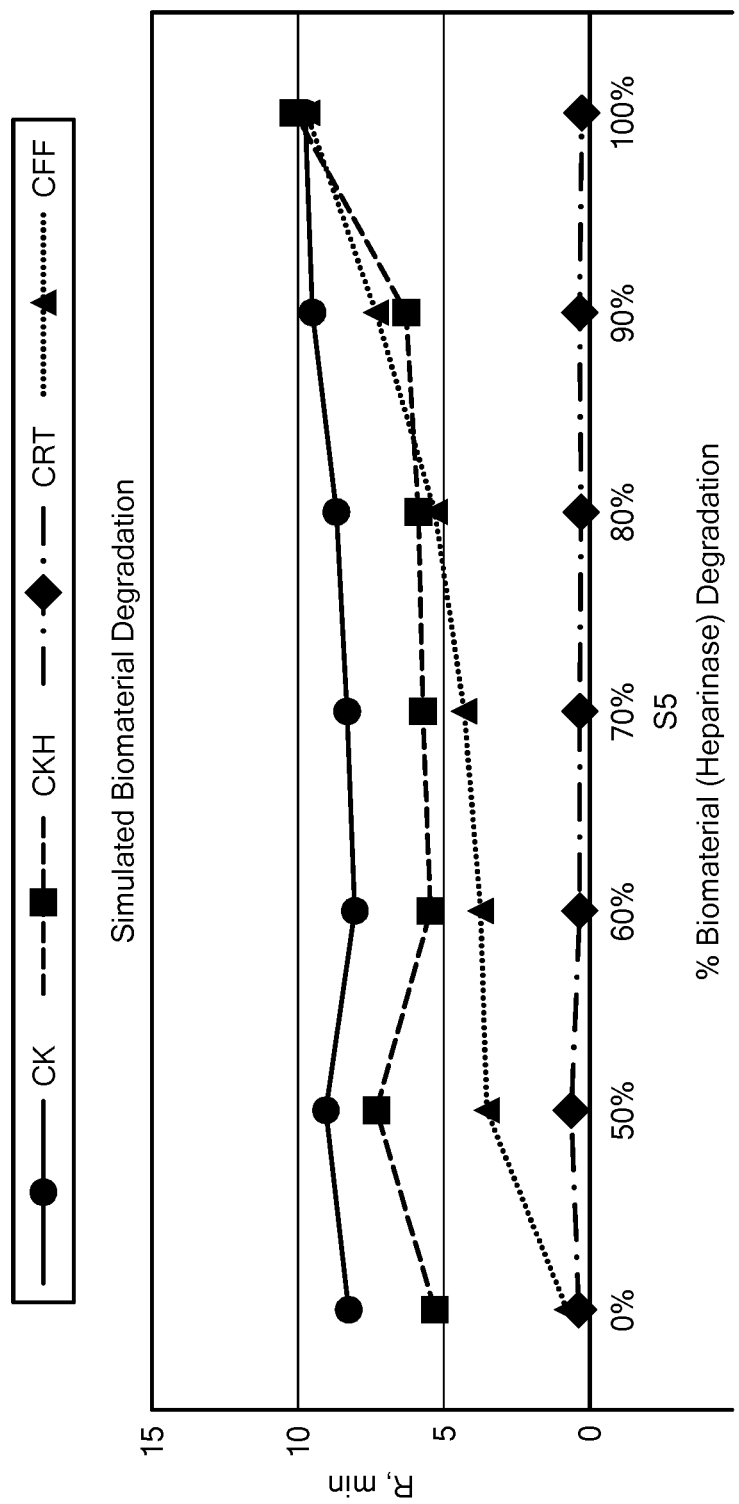
FIG. 3 shows TEG Global Hemostasis cartridge results obtained using quality control formulations described herein under conditions of simulated degradation of heparinase, in accordance with embodiments of the invention.

The quality control formulations can also detect heparinase degradation on the TEG cartridge (see FIG. 3) as evidenced by the CKH R value increasing to match that of the CK K value when the simulated degradation level is greater than 90%.

Various embodiments of the present invention may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

Without limitation, potential subject matter that may be claimed (prefaced with the letter "P" so as to avoid confusion with the actual claims presented below) includes:

P1. A method of preparing a formulation for testing an efficacy of at least one viscoelastic analysis reagent, the formulation having a target bovine citrated plasma concentration, a target human tissue factor concentration, and a target heparin concentration, the method comprising:
  a) determining the target concentration of bovine citrated plasma for the formulation by:
    i) preparing a series of bovine citrated plasma dilutions, the series of bovine citrated plasma dilutions having at least two members,
    ii) measuring a first viscoelastic characteristic for each member of the series of bovine citrated plasma dilutions to obtain a first value for each member of the series of bovine citrated plasma dilutions, said first viscoelastic characteristic having a target value,
    iii) calculating a first linear regression from the first value for each member of the series of bovine citrated plasma dilutions, and
    iv) extrapolating a predicted bovine citrated plasma concentration corresponding to the first viscoelastic characteristic target value from the first linear regression, the predicted bovine citrated plasma concentration being the target bovine citrated plasma concentration;
  b) determining the target concentration of human tissue factor for the formulation by:
    i) preparing a series of human tissue factor dilutions, the series of human tissue factor dilutions having at least two members,
    ii) measuring a second viscoelastic characteristic for each member of the series of human tissue factor dilutions to obtain a second value for each member of the series of human tissue factor dilutions, said second viscoelastic characteristic having a target value,
    iii) calculating a second linear regression from the second value for each member of the series of human tissue factor dilutions, and
    iv) extrapolating a predicted human tissue factor concentration corresponding to the second viscoelastic characteristic target value from the second linear regression, the predicted human tissue factor concentration being the target human tissue factor concentration;
  c) determining the target concentration of heparin for the formulation by:
    i) preparing a series of heparin dilutions, the series of heparin dilutions having at least two members,
    ii) measuring a third viscoelastic characteristic for each member of the series of heparin dilutions to obtain a third value for each member of the series of heparin dilutions, said third viscoelastic characteristic having a target value,
    iii) calculating a third linear regression from the third value for each member of the series of heparin dilutions, and
    iv) extrapolating a predicted heparin concentration corresponding to the third viscoelastic characteristic target value from the third linear regression, the predicted heparin concentration being the target heparin concentration; and
  d) preparing the formulation by combining the bovine citrated plasma, human tissue factor, and heparin together such that the formulation comprises the bovine citrated plasma at the target bovine citrated plasma concentration, the human tissue factor at the target human tissue factor concentration, and the heparin at the target heparin concentration.

P2. The method of preparing a formulation according to claim P1, wherein
  in step (a),
    each member of the series of bovine citrated plasma dilutions has a bovine citrated plasma concentration, the concentration of bovine citrated plasma in any one member of the series of bovine citrated plasma dilutions being different than the concentration of bovine citrated plasma in any other member of the series of bovine citrated plasma dilutions, and
    each member of the series of bovine citrated plasma dilutions has a human tissue factor concentration, the human tissue factor concentration of each member of the series of bovine citrated plasma dilutions being the same;
  in step (b),
    each member of the series of human tissue factor dilutions has a human tissue factor concentration, the concentration of human tissue factor in any one member of the series of human tissue factor dilutions being different than the concentration of human tissue factor in any other member of the series of human tissue factor dilutions,
    each member of the series of human tissue factor dilutions has a bovine citrated plasma concentration, the bovine citrated plasma concentration of each member of the series of human tissue factor dilutions being the target bovine citrated plasma concentration, and
    each member of the series of human tissue factor dilutions has a heparin concentration, the heparin concentration of each member of the series of human tissue factor dilutions being the same; and
  in step (c),
    each member of the series of heparin dilutions has a heparin concentration, the concentration of heparin in any one member of the series of heparin dilutions being different than the concentration of heparin in any other member of the series of heparin dilutions,
    each member of the series of heparin dilutions has a bovine citrated plasma concentration, the bovine citrated plasma concentration of each member of the series of heparin dilutions being the target bovine citrated plasma concentration, and
    each member of the series of heparin dilutions has a human tissue factor concentration, the human tissue factor concentration of each member of the series of heparin dilutions being the target human tissue factor concentration.

P3. The method of preparing a formulation according to claim P1, wherein
  in step (a),
    each member of the series of bovine citrated plasma dilutions has a bovine citrated plasma concentration, the concentration of bovine citrated plasma in any one member of the series of bovine citrated plasma dilutions being different than the concentration of bovine citrated plasma in any other member of the series of bovine citrated plasma dilutions, and each member of the series of bovine citrated plasma dilutions has a human tissue factor concentration, the human tissue factor concentration of each member of the series of bovine citrated plasma dilutions being the same;

in step (c), each member of the series of heparin dilutions has a heparin concentration, the concentration of heparin in any one member of the series of heparin dilutions being different than the concentration of heparin in any other member of the series of heparin dilutions, each member of the series of heparin dilutions has a bovine citrated plasma concentration, the bovine citrated plasma concentration of each member of the series of heparin dilutions being the target bovine citrated plasma concentration, and each member of the series of heparin dilutions has a human tissue factor concentration, the human tissue factor concentration of each member of the series of heparin dilutions being the same; and in step (b), each member of the series of human tissue factor dilutions has a human tissue factor concentration, the concentration of human tissue factor in any one member of the series of human tissue factor dilutions being different than the concentration of human tissue factor in any other member of the series of human tissue factor dilutions, each member of the series of human tissue factor dilutions has a bovine citrated plasma concentration, the bovine citrated plasma concentration of each member of the series of human tissue factor dilutions being the target bovine citrated plasma concentration, and each member of the series of human tissue factor dilutions has a heparin concentration, the heparin concentration of each member of the series of human tissue factor dilutions being the target heparin concentration.

P4. A method of preparing a formulation for testing an efficacy of at least one viscoelastic analysis reagent, the formulation having a target concentration of bovine citrated plasma, a target concentration of human tissue factor, and a target concentration of heparin, the method comprising:

a) determining the target concentration of bovine citrated plasma for the formulation by:
   i) measuring a first viscoelastic characteristic for a bovine citrated plasma dilution to obtain a first value for the bovine citrated plasma dilution, said first viscoelastic characteristic having a target value, and
   ii) determining a predicted bovine citrated plasma concentration based on the first value and corresponding to the first viscoelastic characteristic target value, the predicted bovine citrated plasma concentration being the target bovine citrated plasma concentration;

b) determining the target concentration of human tissue factor for the formulation by:
   i) measuring a second viscoelastic characteristic for a human tissue factor dilution to obtain a second value for the human tissue factor dilution, said second viscoelastic characteristic having a target value, and
   ii) determining a predicted human tissue factor concentration based on the second value and corresponding to the second viscoelastic characteristic target value, the predicted human tissue factor concentration being the target human tissue factor concentration;

c) determining the target concentration of heparin for the formulation by:
   i) measuring a third viscoelastic characteristic for a heparin dilution to obtain a third value for the heparin dilution, said third viscoelastic characteristic having a target value, and
   ii) determining a predicted heparin concentration based on the third value and corresponding to the third viscoelastic characteristic target value, the predicted heparin concentration being the target heparin concentration; and d) preparing the formulation by combining the bovine citrated plasma, the human tissue factor, and the heparin together such that the formulation comprises the bovine citrated plasma at the target bovine citrated plasma concentration, the human tissue factor at the target human tissue factor concentration, the heparin at the target heparin concentration.

P5. A method of preparing a formulation for testing an efficacy of at least one viscoelastic analysis reagent, the formulation having a target bovine citrated plasma concentration, a target human tissue factor concentration, and a target heparin concentration, the method comprising:

a) determining the target bovine citrated plasma concentration for the formulation by:
   i) preparing a series of bovine citrated plasma dilutions, the series of bovine citrated plasma dilutions having at least two members,
   ii) measuring a first viscoelastic characteristic for each member of the series of bovine citrated plasma dilutions to obtain a first value for each member of the series of bovine citrated plasma dilutions, said first viscoelastic characteristic having a target value,
   iii) calculating a first linear regression from the first value for each member of the series of bovine citrated plasma dilutions, and
   iv) extrapolating a predicted bovine citrated plasma concentration corresponding to the first viscoelastic characteristic target value from the first linear regression, the predicted bovine citrated plasma concentration being the target bovine citrated plasma concentration;

b) determining the target human tissue factor concentration and the target heparin concentration for the formulation by:
   i) preparing a human tissue factor dilution set, the human tissue factor dilution set having at least two series of heparin dilutions, each series of heparin dilutions having at least two members, wherein each member of each series of heparin dilutions has a human tissue factor concentration and a heparin concentration,
   ii) measuring a second viscoelastic characteristic for each member of each series of heparin dilutions to obtain a second value for each member of each series of heparin dilutions, said second viscoelastic characteristic having a target value,
   iii) identifying a select member from the human tissue factor dilution set having a measured second viscoelastic characteristic nearer the second viscoelastic characteristic target value than any other member of the human tissue factor dilution set, the human tissue factor concentration of the select member being the target human tissue factor concentration and the heparin concentration of the select member being the target heparin concentration; and c) preparing the formulation by combining the bovine citrated plasma, human tissue factor, and heparin together such that the formulation comprises the bovine citrated plasma at the target bovine citrated plasma concentration, the human tissue factor at the target human tissue factor concentration, and the heparin at the target heparin concentration.

P6. The method of preparing a formulation according to claim P5, wherein in step (a), each member of the series of bovine citrated plasma dilutions has a bovine citrated plasma concentration, the concentration of bovine citrated plasma in any one member of the series of bovine citrated plasma dilutions being different than the concentration of bovine citrated plasma in any other member of the series of bovine citrated plasma dilutions, and each member of the series of bovine citrated plasma dilutions has a human tissue factor concentration, the human tissue factor concentration of each member of the series of bovine citrated plasma dilutions being the same; and in step (b), each member of each series of heparin dilution has a bovine citrated plasma concentration, the bovine citrated plasma concentration of each member of each series of heparin dilutions being the target bovine citrated plasma concentration, the concentration of human tissue factor in any one series of heparin dilutions being different than the concentration of human tissue factor in any other series of heparin dilutions, the concentration of human tissue factor in every member of any one series of heparin dilutions being the same, and the concentration of heparin in any one member of any one series of heparin dilutions being different than the concentration of heparin in any other member of the same series of heparin dilutions.

P7. The method of any one of the preceding claims, wherein the first viscoelastic characteristic is measured using a device for viscoelastic analysis.

P8. The method of any one of the preceding claims, wherein the second viscoelastic characteristic is measured using a device for viscoelastic analysis.

P9. The method of any one of the preceding claims, wherein the third viscoelastic characteristic is measured using a device for viscoelastic analysis.

P10. The method of any one of the preceding claims, wherein the device for viscoelastic analysis is a microfluidic cartridge.

P11. The method of any one of the preceding claims, wherein the first viscoelastic characteristic is MA.

P12. The method of claim P11, wherein the first viscoelastic characteristic target value is about 63.

P13. The method of any one of the preceding claims, wherein the second viscoelastic characteristic is R.

P14. The method of claim P13, wherein the second viscoelastic characteristic target value is about 6.

P15. The method of any one of the preceding claims, wherein the third viscoelastic characteristic is R.

P16. The method of claim P15, wherein the third viscoelastic characteristic target value is about 6.

P17. The method of one of claims P1 and P4, wherein steps (b) and (c) are performed concurrently.

P18. A formulation for testing an efficacy of at least one viscoelastic analysis reagent, the formulation comprising:
60-90% bovine citrated plasma,
0.05-0.20% human tissue factor, and
0.05-0.30 U/ml heparin.

P19. The formulation of claim P18, further comprising a stabilizing agent.

P20. The formulation of claim P19, wherein the stabilizing agent is selected from the group consisting of glycine, HEPES buffer, and combinations thereof.

P21. The formulation of any one claims P18-P20, further comprising a preservative.

P22. The formulation of claim P21, wherein the preservative is sodium azide. P23. The formulation of any one of claims P18-P22, wherein the formulation has a pH of about 7.3 to about 7.9.

P24. The formulation of any one of claims P18-P23, wherein the formulation has a total protein content of greater than about 6.4 g/dL.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method of preparing a formulation for testing an efficacy of at least one viscoelastic analysis reagent, the formulation having a target bovine citrated plasma concentration, a target human tissue factor concentration, and a target heparin concentration, the method comprising:

a) determining the target concentration of bovine citrated plasma for the formulation by:

i) preparing a series of bovine citrated plasma dilutions, the series of bovine citrated plasma dilutions having at least two members, ii) measuring a first viscoelastic characteristic for each member of the series of bovine citrated plasma dilutions to obtain a first value for each member of the series of bovine citrated plasma dilutions, said first viscoelastic characteristic having a target value, iii) calculating a first linear regression from the first value for each member of the series of bovine citrated plasma dilutions, and iv) extrapolating a predicted bovine citrated plasma concentration corresponding to the first viscoelastic characteristic target value from the first linear regression, the predicted bovine citrated plasma concentration being the target bovine citrated plasma concentration;

b) determining the target concentration of human tissue factor for the formulation by:

i) preparing a series of human tissue factor dilutions, the series of human tissue factor dilutions having at least two members, ii) measuring a second viscoelastic characteristic for each member of the series of human tissue factor dilutions to obtain a second value for each member of the series of human tissue factor dilutions, said second viscoelastic characteristic having a target value, iii) calculating a second linear regression from the second value for each member of the series of human tissue factor dilutions, and iv) extrapolating a predicted human tissue factor concentration corresponding to the second viscoelastic characteristic target value from the second linear regression, the predicted human tissue factor concentration being the target human tissue factor concentration;

c) determining the target concentration of heparin for the formulation by:

i) preparing a series of heparin dilutions, the series of heparin dilutions having at least two members, ii) measuring a third viscoelastic characteristic for each member of the series of heparin dilutions to obtain a third value for each member of the series of heparin dilutions, said third viscoelastic characteristic having a target value, iii) calculating a third linear regression from the third value for each member of the series of heparin dilutions, and iv) extrapolating a predicted heparin concentration corresponding to the third viscoelastic characteristic target value from the third linear regression, the predicted heparin concentration being the target heparin concentration; and d) preparing the formulation by combining the bovine citrated plasma, human tissue factor, and heparin together such that the formulation comprises the bovine citrated plasma at the target bovine citrated plasma concentration, the human tissue factor at the target human tissue factor concentration, and the heparin at the target heparin concentration.

2. The method of preparing a formulation according to claim 1, wherein in step (a),
each member of the series of bovine citrated plasma dilutions has a bovine citrated plasma concentration, the concentration of bovine citrated plasma in any one member of the series of bovine citrated plasma dilutions being different than the concentration of bovine citrated plasma in any other member of the series of bovine citrated plasma dilutions, and each member of the series of bovine citrated plasma dilutions has a human tissue factor concentration, the human tissue factor concentration of each member of the series of bovine citrated plasma dilutions being the same;

in step (b),
each member of the series of human tissue factor dilutions has a human tissue factor concentration, the concentration of human tissue factor in any one member of the series of human tissue factor dilutions being different than the concentration of human tissue factor in any other member of the series of human tissue factor dilutions, each member of the series of human tissue factor dilutions has a bovine citrated plasma concentration, the bovine citrated plasma concentration of each member of the series of human tissue factor dilutions being the target bovine citrated plasma concentration, and each member of the series of human tissue factor dilutions has a heparin concentration, the heparin concentration of each member of the series of human tissue factor dilutions being the same; and in step (c),
each member of the series of heparin dilutions has a heparin concentration, the concentration of heparin in any one member of the series of heparin dilutions being different than the concentration of heparin in any other member of the series of heparin dilutions, each member of the series of heparin dilutions has a bovine citrated plasma concentration, the bovine citrated plasma concentration of each member of the series of heparin dilutions being the target bovine citrated plasma concentration, and each member of the series of heparin dilutions has a human tissue factor concentration, the human tissue factor concentration of each member of the series of heparin dilutions being the target human tissue factor concentration.

3. The method of preparing a formulation according to claim 1, wherein in step (a),
each member of the series of bovine citrated plasma dilutions has a bovine citrated plasma concentration, the concentration of bovine citrated plasma in any one member of the series of bovine citrated plasma dilutions being different than the concentration of bovine citrated plasma in any other member of the series of bovine citrated plasma dilutions, and each member of the series of bovine citrated plasma dilutions has a human tissue factor concentration, the human tissue factor concentration of each member of the series of bovine citrated plasma dilutions being the same;

in step (c),
each member of the series of heparin dilutions has a heparin concentration, the concentration of heparin in any one member of the series of heparin dilutions being different than the concentration of heparin in any other member of the series of heparin dilutions, each member of the series of heparin dilutions has a bovine citrated plasma concentration, the bovine citrated plasma concentration of each member of the series of heparin dilutions being the target bovine citrated plasma concentration, and each member of the series of heparin dilutions has a human tissue factor concentration, the human tissue factor concentration of each member of the series of heparin dilutions being the same; and in step (b),
each member of the series of human tissue factor dilutions has a human tissue factor concentration, the concentration of human tissue factor in any one member of the series of human tissue factor dilutions being different than the concentration of human tissue factor in any other member of the series of human tissue factor dilutions, each member of the series of human tissue factor dilutions has a bovine citrated plasma concentration, the bovine citrated plasma concentration of each member of the series of human tissue factor dilutions being the target bovine citrated plasma concentration, and each member of the series of human tissue factor dilutions has a heparin concentration, the heparin concentration of each member of the series of human tissue factor dilutions being the target heparin concentration.

4. A method of preparing a formulation for testing an efficacy of at least one viscoelastic analysis reagent, the formulation having a target concentration of bovine citrated plasma, a target concentration of human tissue factor, and a target concentration of heparin, the method comprising:

a) determining the target concentration of bovine citrated plasma for the formulation by:
  i) measuring a first viscoelastic characteristic for a bovine citrated plasma dilution to obtain a first value for the bovine citrated plasma dilution, said first viscoelastic characteristic having a target value, and
  ii) determining a predicted bovine citrated plasma concentration based on the first value and corresponding to the first viscoelastic characteristic target value, the predicted bovine citrated plasma concentration being the target bovine citrated plasma concentration;

b) determining the target concentration of human tissue factor for the formulation by:
  i) measuring a second viscoelastic characteristic for a human tissue factor dilution to obtain a second value for the human tissue factor dilution, said second viscoelastic characteristic having a target value, and
  ii) determining a predicted human tissue factor concentration based on the second value and corresponding to the second viscoelastic characteristic target value, the predicted human tissue factor concentration being the target human tissue factor concentration;

c) determining the target concentration of heparin for the formulation by:
  i) measuring a third viscoelastic characteristic for a heparin dilution to obtain a third value for the heparin dilution, said third viscoelastic characteristic having a target value, and
  ii) determining a predicted heparin concentration based on the third value and corresponding to the third viscoelastic characteristic target value, the predicted heparin concentration being the target heparin concentration; and d) preparing the formulation by combining the bovine citrated plasma, the human tissue factor, and the heparin together such that the formulation comprises the bovine citrated plasma at the target bovine citrated plasma concentration, the human tissue factor at the target human tissue factor concentration, the heparin at the target heparin concentration.

5. The method of claim 1, wherein the first viscoelastic characteristic is measured using a device for viscoelastic analysis.

6. The method of claim 1, wherein the second viscoelastic characteristic is measured using a device for viscoelastic analysis.

7. The method of claim 1, wherein the third viscoelastic characteristic is measured using a device for viscoelastic analysis.

8. The method of claim 1, wherein the device for viscoelastic analysis is a microfluidic cartridge.

9. The method of claim 1, wherein the first viscoelastic characteristic is MA (maximum amplitude in mm).

10. The method of claim 9, wherein the first viscoelastic characteristic target value is about 63.

11. The method of claim 1, wherein the second viscoelastic characteristic is R (clot initiation time).

12. The method of claim 11, wherein the second viscoelastic characteristic target value is about 6.

13. The method of claim 1, wherein the third viscoelastic characteristic is R (clot initiation time).

14. The method of claim 13, wherein the third viscoelastic characteristic target value is about 6.

15. The method of claim 1, wherein steps (b) and (c) are performed concurrently.

16. The method of claim 4, wherein steps (b) and (c) are performed concurrently.

17. A formulation for testing an efficacy of at least one viscoelastic analysis reagent, the formulation comprising:
  60-90% bovine citrated plasma,
  0.05-0.20% human tissue factor, and
  0.05-0.30 U/ml heparin.

18. The formulation of claim 17, wherein the formulation has a pH of about 7.3 to about 7.9.

19. The formulation of claim 17, wherein the formulation has a total protein content of greater than about 6.4 g/dL.

20. The formulation of claim 17, further comprising a stabilizing agent, wherein the stabilizing agent is selected from the group consisting of glycine, HEPES buffer, and combinations thereof.

* * * * *